United States Patent [19]
Hashimoto et al.

[11] 4,083,223
[45] Apr. 11, 1978

[54] NONDESTRUCTIVE INSPECTION METHOD FOR SPOT-WELDED JOINTS

[75] Inventors: Masaru Hashimoto, Yokosuka; Masaya Ogata, Yokosuia, both of Japan

[73] Assignee: Nissan Motor Company, Limited, Yokohama, Japan

[21] Appl. No.: 740,472

[22] Filed: Nov. 10, 1976

[30] Foreign Application Priority Data

Nov. 11, 1975 Japan .............................. 50-135425

[51] Int. Cl.² ............................................. G01N 25/72
[52] U.S. Cl. ................................................... 73/15 FD
[58] Field of Search ............... 73/15 R, 15 A, 15 FD; 340/248 W, 248 F

[56] References Cited

U.S. PATENT DOCUMENTS

| | | | |
|---|---|---|---|
| 3,206,603 | 9/1965 | Mauro | 73/15 |
| 3,406,272 | 10/1968 | Ehrlich | 340/248 |
| 3,427,861 | 2/1969 | Maley | 73/15 |
| 3,434,332 | 3/1969 | Maley | 73/15 |
| 3,566,669 | 3/1971 | Lawrence et al. | 73/15 |
| 3,599,474 | 8/1977 | Brown et al. | 73/1 |

OTHER PUBLICATIONS

Katzoff, "The Surface-Tension Method of Visually Inspecting Honeycomb-Core Sandwich Plate" in Non Destructive 4/60 pp. 114–118.

Malim, "Infrared Scans for Inner Defects" in Iron Age Reprint, 5/65.

*Primary Examiner*—Herbert Goldstein
*Attorney, Agent, or Firm*—Bacon & Thomas

[57] ABSTRACT

The quality of joints formed by spot welding, particularly the diameters of the individual nuggets, can accurately and nondestructively be inspected by heating or cooling one of the welded members and measuring the distribution of the surface temperature of the other member because of a maximal heat conduction at each nugget. The surface temperature distribution may be measured merely linearly since the width of a peak on the temperature-distance curve depends on the diameter of a nugget.

3 Claims, 6 Drawing Figures

NONDESTRUCTIVE INSPECTION METHOD FOR SPOT-WELDED JOINTS

BACKGROUND OF THE INVENTION

1. Field of the Invention

This invention relates to a thermal test method for nondestructive inspection of the quality of welds formed by spot welding, particularly of the diameters of the individual nuggets.

2. Description of the Prior Art

The strength of a weld joint formed by spot welding is measured by making a tension test on the welded members with a tension tester for materials. However, the strength of a spot-welded joint can fairly accurately be estimated by examining the size and fusion condition of the nugget in each weld zone. For visual inspection of the size and appearance of the nuggets, welded members are split with an wedge-shaped implement such as a chisel. Alternatively, the welded members are cut in two across each nugget. These destructive test methods are naturally of use only in sampling inspection.

Practically the one and only method for the nondestructive inspection, which may be either sampling inspection 100% inspection, of spot-welded joints is ultrasonic testing. It is difficult, however, to accurately estimate the size of each nugget by ultrasonic testing. The presence of the impressions of the electrode tips for spot welding on the surfces of the welded members obstructs a smooth scanning of a ultrasonic impulse over the weld whether the testing is conducted by the immersion method or by the contact method. In the case of the contact testing method, the accuracy of the inspection is influenced by the shape and size of the tracer of the testing instrument, too.

SUMMARY OF THE INVENTION

It is an object of the present invention to provide a method of accurately and nondestructively inspecting joints formed by spot welding, which method is free from the above described disadvantages involved in conventional ultrasonic testing methods.

According to the invention, the quality of a spot-welded joint including the size of each nugget is inspected by varying substantially uniformly the temperature of one of the welded members relatively to the other at least in a portion including the joint and measuring the distribution of temperature on a surface of the latter member remote from the former member in a region including the joint.

The temperature variation of one of the welded members is effected conveniently by heating buy may alternatively be done by cooling. This inspection method is based on the fact that the heat conduction through the joint occurs at a maximal rate through each nugget.

BRIEF DESCRIPTION OF THE DRAWING

The invention will fully be understood from the following detailed description of preferred embodiments with reference to the accompanying drawings, wherein.

EXAMPLE 1

Figure 1:
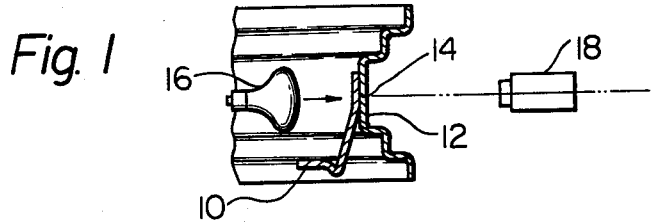
FIG. 1 is a schematic presentation of an exemplary arrangement of a spot-welded specimen and testing instruments in an inspection method according to the invention.
Figure 2:
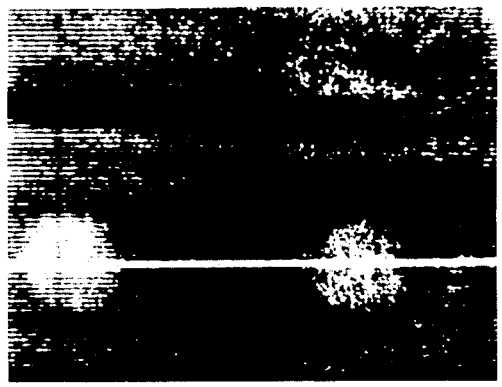
FIG. 2 is a photograph as a record of the surface temperature distribution taken by the method of FIG. 1, wherein white regions indicate high temperature regions.

Referring to FIG. 1, two 3.2 mm thick steel sheets 10 and 12 were joined together by spot welding. The reference numeral 14 indicates nuggets in the welded joint. To heat one (10) of the welded steel sheets 10, 12, a 500-watt infrared lamp 16 which had a shape suitable to flood lighting was placed opposite to the outer surface of the steel sheet 10 at a distance of 80 cm. The steel sheet 10 was uniformly heated in a region including the welded joint by lighting the lamp 16 for 3 sec. Immediately, the distribution of the temperature on the outer surface of the other steel sheet 12, in a region at the back of the irradiated region of the steel sheet 10, was measured by means of a thermocamera 18, and a light-and-shade photograph in black and white as shown in FIG. 2 was obtained. White regions on this photograph indicate high temperature regions of the outer surface of the steel sheet 12. Since the heat conduction from the heated steel sheet 10 to the other steel sheet 12 through the nuggets 14 occurs at a higher rate than through the remaining part of the joint, the photograph clearly indicates the presence of two nuggets 14 as two white circles. These white circles may be regarded as a parallel projection of the nuggets 14. The diameter of each nugget can be known by measuring the diameter of each white circle on the photograph. At the same time, the fusion condition of the nuggets can be estimated from the brightness or whiteness of the white circles.

The distribution of the surface temperature on the steel sheet 12 need not necessarily measured two-dimentionally over a certain area to give a photograph or an equivalent chart. We have performed a one-dimentional measurement on the specimen 10, 12 of FIG. 1 immediately after a 3 sec irradiation by the lamp 16 by scanning with a thermograph along a line on the outer surface of the steel sheet 12 corresponding to a line connecting the centers of the two white circles on the photograph of FIG. 2. The result of the measurement is shown by the temperature-distance curve of FIG. 3. As seen, two distinct temperature peaks appear in the positions of the two nuggets. The condition of each nugget 14 can be estimated from the temperature at the summit of each of these peaks on the curve of FIG. 3. However, the diameter of the nugget 14 can more accurately be known from the width of the peak. Referring to an explanatory temperature-distance curve of FIG. 4, the width of a temperature peak indicating the presence of a nugget is herein defined as a half-height width W of the peak at half of the height H of the peak.

EXAMPLE 2

Figure 5:
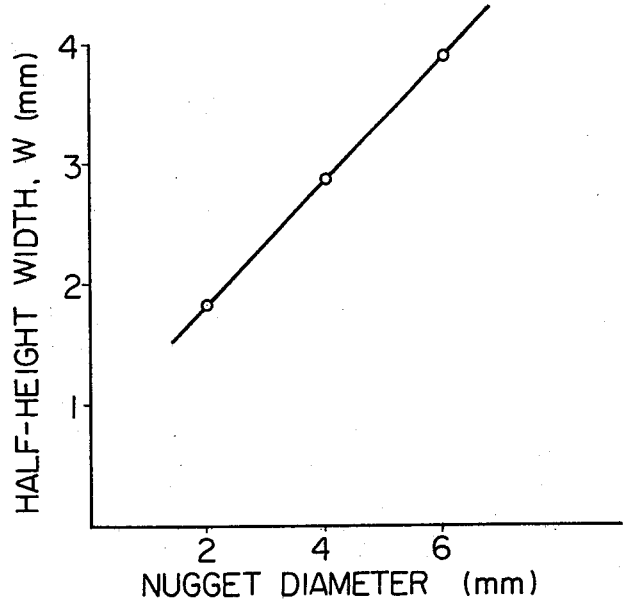
FIG. 5 is a graph showing an example of the relationship between the width of the aforementioned temperature peak and the diameter of a nugget.

Spot welding was performed to join two 3.2 mm thick steel sheets at several different welding currents so that differently sized nuggets might be formed in the joint. One of the welded steel sheets was subjected to heating in the same manner as in Example 1, and the surface temperature distibution on the other steel sheet was measured by the above described linear (one-dimentional) scanning method. The above defined half-height width W was measured for each of the temperature peaks on the obtained temperature-distance curve. Thereafter, the diameter of each nugget was measured by cutting the welded steel sheets. FIG. 5 shows the thus confirmed relationship between the actual diameter of each nugget and the half-height width W on the temperature-distance curve. As seen, there is a clear and approximately linear correlation between the nugget diameter and the half-height width W.

Figure 3:
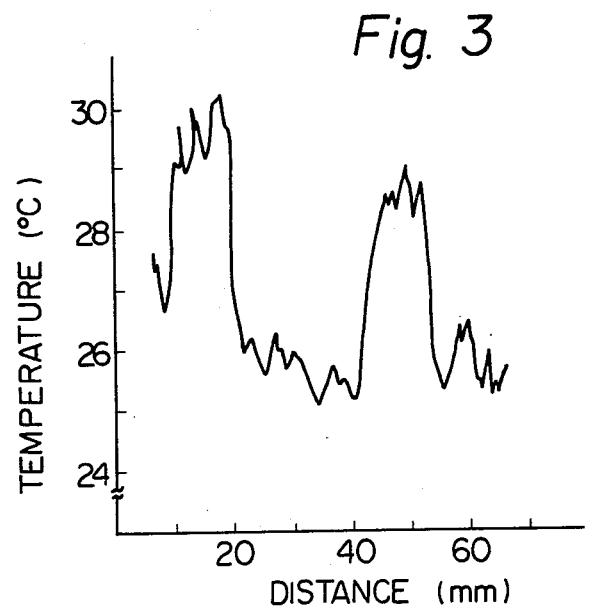
FIG. 3 is a graph as the record of a one-dimentional measurement of the surface temperature distribution made on the same specimen as in taking the photograph of FIG. 2.
Figure 4:
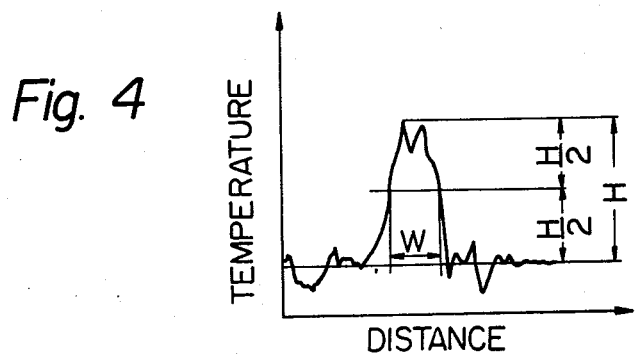
FIG. 4 is a temperature distribution graph presented for the explanation of the definition of the width of a peak temperature which is employed as an indication of the diameter of a nugget in a method of the invention.

In practical applications of a method according to the invention, the diameter of each nugget in a joint of a particular design can accurately and nondestructively be estimated by initially preparing a conversion curve as shown in FIG. 5 for a limited number of the products and thereafter preparing a temperature-distance curve as shown in FIG. 3 for each specimen.

Usually it is convenient to cause a temperature variation for one of the welded members by heating as in the above examples. It is of course possible, however, to cool one of the welded members and measure the surface temperature distribution for the other member.

When three sheet members are spot-welded in a pile, the inspection according to the invention may be performed by heating (or cooling) the middle member and measuring the surface temperature distribution for both of the remaining two members thereby to inspect the nuggets formed on both sides of the middle member.

Figure 6:
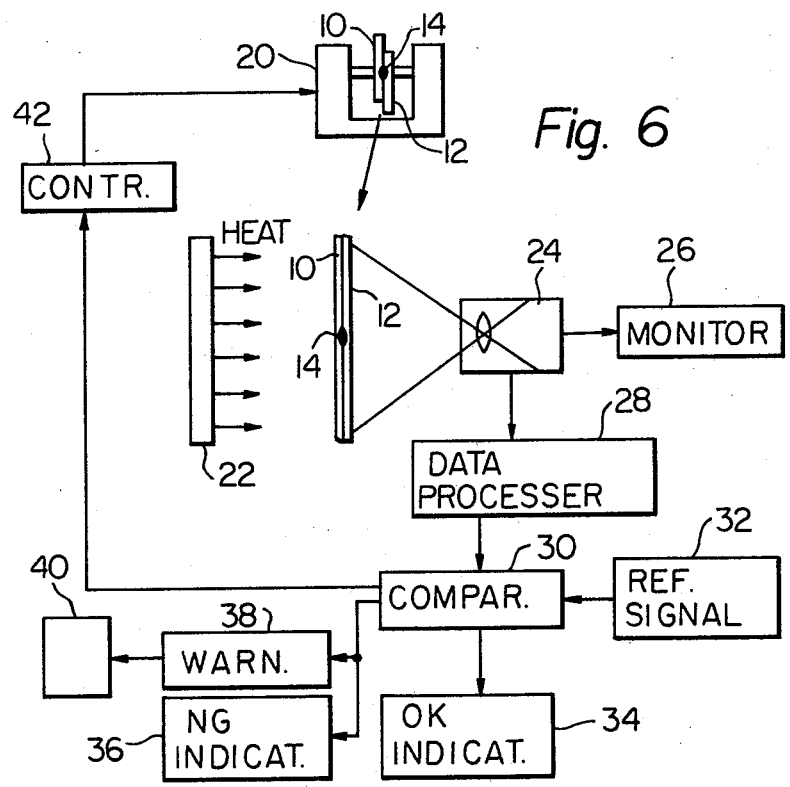
FIG. 6 is a block diagram of a spot welding system including an inspection apparatus for performing a method according to the invention and a sorting apparatus.

Since the inspection method according to the invention is nondestructive and gives quantittative data, it is possible to construct a feedback control system for a spot welding operation by combining a thermal measurement apparatus with an electrical feedback control circuit and a sorting apparatus. FIG. 6 shows an example of such a control system for a spot welding machine 20. Each of the welded products, represented by the welded members 10, 12, is transferred from the welding machine 20 to an inspection site, where a heating device 22 is arranged to heat one (10) of the welded members 10, 12 in a region including the nuggets 14 and a temperature distribution measurement instrument 24 such as a thermograph or a pyrometer opposite the other member 12. The output of the measuring instrument 24 is transmitted to both a monitoring instrument 26 and a data processor 28. The data processor 28 and a reference signal circuit 32 are connected to a comparison and judgement circuit 30 which can provide its output to either an OK indicator 34 or an NG indicator 36. A warning device 38 and an actuator of a machine 40 which can reject unacceptable products are connected in parallel with the NG indicator 36. The welding machine 20 is provided with a welding condition control circuit 42, and the output of the comparison and judgement circuit 30 is applied to this control circuit 42, too.

The welding machine 20 is operated under a preset welding condition. At the inspection site, the member 10 of the welded product is heated under a predetermined heating condition, and the surface temperature distribution is measured on the surface of the other member 12 with the measurement instrument 24. The half-height width W in the temperature distribution data can visually be observed by means of the monitoring instrument 26. The data processer 28 provides an output representing the half-height width W implied in the temperature distribution signal from the measurement instrument 24. The reference signal circuit 32 is adjusted to provide a reference signal of a predetermined amplitude representing a value of the half-height width W corresponding to a nugget diameter employed as the criterion for the acceptance and rejection of the inspected products. When the comparison of the output of the data processer 28 with the reference signal confirmed that the measured half-height width W, i.e. the nugget diameter, is larger than the critical value, the circuit 30 provides its output only to the OK indicator 34. If the measured nugget size is smaller than the critical value, the NG indicator 36 and the warning device 38 are actuated by the output of the comparison and judgement circuit 30. Besides, the machine 40 is actuated and rejected the inspected product from the product line. At the same time, the result of the comparison in the circuit 30 is transmitted to the control circuit 42 as a feedback signal, so that the welding condition can properly be varied when the welding machine 20 produces an unacceptable product.

Thus, the method according to the invention not only enables an easy and accurate inspection of spot-welded joints but also serves as a key for the automation of a spot-welding operation.

What is claimed is:

1. A method of inspecting a joint formed by spot-welding of members which comprises the steps of:
    varying substantially uniformly the temperature of one of the said welded members relative to the other welded members in a region including at least the joint; and
    measuring the distribution of temperature on a surface of the said other welded members in a region including the joint, said temperature distribution being measured one dimensionally across a parallel projection of a nugget formed in the joint on said surface,
    said measurement step further comprising the steps of:
    preparing a temperature-distance curve representing said temperature distribution;
    measuring the width of a temperature peak on said curve at half of the height of said temperature peak; and
    estimating the diameter of said nugget from said width based on a preliminarily examined relationship between said width and said diameter.

2. A method as claimed in claim 1, wherein the temperature of said one of the welded members is raised.

3. The process as defined by claim 1 wherein the temperature of said welding members is lowered.

* * * * *